(12) United States Patent
Han et al.

(10) Patent No.: US 11,786,629 B2
(45) Date of Patent: Oct. 17, 2023

(54) POLYVINYL ALCOHOL/SODIUM ALGINATE/HYDROXYAPATITE COMPOSITE FIBROUS MEMBRANE, AND PREPARATION METHOD AND APPLICATION THEREOF

(71) Applicant: WUHAN UNIVERSITY OF TECHNOLOGY, Hubei (CN)

(72) Inventors: Yingchao Han, Hubei (CN); Gang Zhao, Hubei (CN); Honglian Dai, Hubei (CN)

(73) Assignee: WUHAN UNIVERSITY OF TECHNOLOGY, Hubei (CN)

( * ) Notice: Subject to any disclaimer, the term of this patent is extended or adjusted under 35 U.S.C. 154(b) by 895 days.

(21) Appl. No.: 16/067,820

(22) PCT Filed: Jan. 18, 2017

(86) PCT No.: PCT/CN2017/071507
§ 371 (c)(1),
(2) Date: Jul. 3, 2018

(87) PCT Pub. No.: WO2018/129761
PCT Pub. Date: Jul. 19, 2018

(65) Prior Publication Data
US 2021/0205491 A1 Jul. 8, 2021

(30) Foreign Application Priority Data
Jan. 16, 2017 (CN) .......................... 201710028626.7

(51) Int. Cl.
| | | |
|---|---|---|
| A61L 15/22 | (2006.01) | |
| D04H 1/4382 | (2012.01) | |
| A61F 13/00 | (2006.01) | |
| A61L 15/18 | (2006.01) | |
| A61L 15/44 | (2006.01) | |
| C08L 5/04 | (2006.01) | |
| C08L 29/04 | (2006.01) | |

(52) U.S. Cl.
CPC ...... *A61L 15/225* (2013.01); *A61F 13/00987* (2013.01); *A61L 15/18* (2013.01); *A61L 15/44* (2013.01); *D04H 1/43825* (2020.05); *A61L 2430/34* (2013.01); *C08L 5/04* (2013.01); *C08L 29/04* (2013.01)

(58) Field of Classification Search
None
See application file for complete search history.

(56) References Cited

FOREIGN PATENT DOCUMENTS

| CN | 103171153 | | 6/2013 |
| CN | 104117341 A | * | 10/2014 |
| CN | 106178065 A | * | 12/2016 |

OTHER PUBLICATIONS

Wang, Hongli et al. "Research on Structure and properties of Nano-hydroxyapatite/Polyvinyl Alcohol/Sodium Alginate Composite Hydrogel", Journal of Chengdu (Natural Science Edition), Sep. 2012, pp. 211-214 (Year: 2012).*
Sohail Shahzad, Chitosan-based electrospun nanofibrous mats, hydrogels and cast films: novel anti-bacterial wound dressing matrices, Feb. 26, 2015, J Mater Sci: Mater Med, 26:136 (Year: 2015).*
Jin-Hwan Chung, Synthesis, characterization, biocompatibility of hydroxyapatite-natural polymers nanocomposites for dentistry applications, Aug. 11, 2014, Artificial Cells, Nanomedicine, and Biotechnology, 44:1, 277-284 (Year: 2014).*
Viness Pillay, A Review of the Effect of Processing Variables on the Fabrication of Electrospun Nanofibers for Drug Delivery Applications, 2013, Hindawi Publishing Corporation, Journal of Nanomaterials, vol. 2013 (Year: 2013).*
Anssar Houdali, Immobilizing hydroxyapatite microparticles on poly(lactic acid) nonwoven scaffolds using layer-by-layer deposition, Sep. 30, 2016, Textile Research Journal, vol. 87(16), 2028-2038 (Year: 2016).*
Wang et al., "Research on Structure and Properties of Nano-hydroxyapatite/ Polyvinyl Alcohol /Sodium Alginate Composite Hydrogel," Journal of Chengdu University (Natural Science Edition), Sep. 2012, pp. 211-214.
Wang et al., "Preparation and Characterization of a Nano-hydoxyapatite/ SodiumAlginate-Polyvinyl Alcohol Composite Scaffold," Journal of Southwest University (Natural Science Edition), Jan. 2013, pp. 160-164.
Wang et al., "Preparation and characterisation of nanohydroxyapatite-sodium alginate-polyvinyl alcohol composite scaffold," Materials Research Innovations, Nov. 2010, pp. 375-380.
Yang et al., "Preparation and properties of sodium alginate/poly (vinyl alcohol)/hydroxyapatite composite fiber," Journal of Dalian Polytechnic University, Sep. 2012, pp. 362-366.
Peilong Ni et al., "Electrospun preparation and biological properties in vitro of polyvinyl alcohol/sodium alginate/nano-hydroxyapatite composite fiber membrane", Colloids and Surfaces B: Biointerfaces, Jan. 1, 2019, pp. 171-177.

* cited by examiner

*Primary Examiner* — Abigail Vanhorn
*Assistant Examiner* — Ali S Saeed
(74) *Attorney, Agent, or Firm* — JCIPRNET

(57) ABSTRACT

The present invention relates to a polyvinyl alcohol/sodium alginate/hydroxyapatite composite fibrous membrane, and a preparation method and an application thereof. The preparation method of the composite fibrous membrane includes the following steps: firstly, reacting a diammonium hydrogen phosphate with a calcium nitrate to prepare a hydroxyapatite, and performing ultrasonic dispersion on the hydroxyapatite with a sodium alginate to form a stable hydroxyapatite suspension; separately preparing a sodium alginate solution of which the mass fraction is 2% and a polyvinyl alcohol solution of which the mass fraction is 18% using the above stable hydroxyapatite suspension; and finally, proportionally and uniformly mixing the two solutions, and performing electrospinning.

12 Claims, 6 Drawing Sheets

POLYVINYL ALCOHOL/SODIUM ALGINATE/HYDROXYAPATITE COMPOSITE FIBROUS MEMBRANE, AND PREPARATION METHOD AND APPLICATION THEREOF

CROSS-REFERENCE TO RELATED APPLICATION

This application is a 371 application of International PCT application serial no. PCT/CN2017/071507, filed on Jan. 18, 2017, which claims the priority benefit of Chinese application no. 201710028626.7, filed on Jan. 16, 2017. The entirety of each of the above-mentioned patent applications is hereby incorporated by reference herein and made a part of this specification.

BACKGROUND

Technical Field

The present invention relates to the technical field of electrospinning, particularly a polyvinyl alcohol/sodium alginate/hydroxyapatite composite fibrous membrane, and a preparation method and application thereof.

Description of Related Art

A soft tissue injury is a very common type of lesion at present. Soft tissues people often say refer to skin, subcutaneous tissues, muscles, tendons, ligaments, joint capsules, synovial bursae, nerves, blood vessels and the like of the human body. Skin, for example, can protect various tissues and organs in the body from external mechanical and pathogenic damage, and skin injuries and defects may cause a series of pathophysiologic problems. For a large area of skin defects, in addition to autologous skin graft repair, artificial medical dressings may also protect damaged skin to provide a good physiological repair environment for wound healing, and do not have the problem of limited autologous skin sources, thus having broad application prospects.

An ideal artificial medical dressing not only is to cover the wound, but also must: be non-toxic, have favorable biocompatibility, be convenient to use, do not need frequent replacement, be capable of preventing bacterial invasion, be capable of removing exudate and keeping the wound moist, and have a certain bioactivity to promote wound repair. Generally, according to the materials, the artificial medical dressings are divided into traditional dressings, natural dressings, synthetic dressings and medicinal dressings. Considering all the advantages and disadvantages of these dressings, it is an urgent need for people at present to organically combine favorable properties of natural polymer and synthetic polymer materials by an electrospinning method to prepare a composite fiber membrane with biocompatibility and bioactivity as a soft tissue injury repair dressing.

Electrospinning technology originated in the 1930s and has been flourishing in the last 20 years. This technology is low in manufacturing cost and simple in technique, can rapidly obtain a wide variety of ultrafine fibers with diameters ranging from several nanometers to several micrometers, and thus, is recognized as one of the most important methods having the potential for mass production of nanofiber materials. The electrospun nanofiber material with a three-dimensional spatial structure not only has the characteristics of nanoparticles such as small size, large specific surface area and the like, but also has the advantages of favorable mechanical stability, small fibrous membrane pore diameter, high porosity, good fiber continuity and the like. The electrospun nanofiber material facilitates cell adhesion, migration and proliferation, further replicates the three-dimensional structure of tissue, and promotes cell differentiation to different cell lines.

Sodium alginate is a safe and non-toxic natural polymer material, has high hygroscopicity, hemostatic property and gelating property, has the advantages of promoting wound healing, inhibiting bacteria, and reducing local pain and scar formation, and provides a favorable microenvironment for injured skin repair. As a synthetic polymer with good biocompatibility, polyvinyl alcohol is a commonly used raw material for electrospinning due to outstanding film forming and filament forming properties. Hydroxyapatite, as an inorganic component in human bones, has high biocompatibility and bioactivity, high cell adhesion property and high cell affinity; moreover, calcium ions and phosphate ions produced by degradation of hydroxyapatite can provide nutrients for cell growth. However, sodium alginate is a polyelectrolyte, single-component sodium alginate fibrous membrane can hardly be fabricated by the electrospinning method; moreover, the degradation of alginate will lead to weak acidic microenvironment. Whereas, hydroxyapatite is a weak alkaline inorganic substance. Therefore, the blend spinning of the above three materials is considered to achieve the complementary advantages.

The present invention realizes uniform dispersion of hydroxyapatite nanoparticles in the composite fibrous membrane, and the obtained composite fibrous membrane combines the biocompatibility of the natural and synthetic polymers with the bioactivity of the hydroxyapatite nanoparticles. The obtained composite fibrous membrane can be used as a soft tissue injury repair dressing and can load an antibiotic or growth factor to improve the repair effect of soft tissue injuries.

SUMMARY

In order to solve the problems that the comprehensive properties of the existing composite fibrous membrane dressings are not excellent enough and the spinning raw material, hydroxyapatite nanoparticles, are prone to agglomeration and uneven dispersion, the present invention provides a polyvinyl alcohol/sodium alginate/hydroxyapatite composite fibrous membrane and a preparation method. The composite fibrous membrane combines the biocompatibility of the natural and synthetic polymers with the bioactivity of the hydroxyapatite nanoparticles. The obtained composite fibrous membrane is an excellent soft tissue injury repair dressing and can carry an antibiotic or growth factor to enhance the repair effect of soft tissue injuries. In order to achieve the goals, the present invention adopts the following technical solution:

A polyvinyl alcohol/sodium alginate/hydroxyapatite composite fibrous membrane is disclosed, wherein the mass ratio of polyvinyl alcohol to sodium alginate to hydroxyapatite is 1:(0.01-0.0563):(0.01-0.0834).

A preparation method of the polyvinyl alcohol/sodium alginate/hydroxyapatite composite fibrous membrane includes the following steps: (a) reacting diammonium hydrogen phosphate with calcium nitrate to prepare hydroxyapatite, dispersing hydroxyapatite in deionized water, adding sodium alginate and uniformly mixing the mixture to obtain a sodium-alginate-stabilized hydroxyapatite suspension; (b) separately preparing a hydroxyapatite-containing sodium alginate solution and a hydroxyapatite-containing polyvinyl alcohol solution using the sodium-alginate-stabilized hydroxyapatite suspension prepared in the step (a); and (c) proportionally and uniformly mixing the hydroxyapatite-containing sodium alginate solution and the hydroxyapatite-containing polyvinyl alcohol solution to obtain a spinning solution containing hydroxyapatite, sodium alginate and polyvinyl alcohol, and performing electrospinning to obtain the composite fibrous membrane.

In the above-mentioned solution, the process for preparing hydroxyapatite specifically includes the following steps: quickly pouring a diammonium hydrogen phosphate water solution into a calcium nitrate water solution according to a Ca/P mole ratio of 1.67, dropwisely adding ammonia water into the mixture to regulate the pH of the solution to 9-10, stirring the mixture uniformly, allowing the mixture to react at 80° C., performing centrifugal separation, and performing water washing several times to obtain the hydroxyapatite white precipitate.

Preferably, the concentration of the diammonium hydrogen phosphate water solution is 0.001-0.1 mol/L, and the concentration of the calcium nitrate water solution is 0.00668-0.167 mol/L.

In the above-mentioned solution, ultrasonic dispersion is used in the preparation of the hydroxyapatite suspension, the concentration of sodium alginate in the suspension is 0.04-0.15 mg/mL, and the concentration of hydroxyapatite is 1.67-16.7 mg/mL.

In the above-mentioned solution, the sodium alginate solution of which the mass fraction is 2% and the polyvinyl alcohol solution of which the mass fraction is 18% are prepared at 60-80° C.

In the above-mentioned solution, the volume ratio of the hydroxyapatite-containing sodium alginate solution to the hydroxyapatite-containing polyvinyl alcohol solution during the mixing is (0.1-1):(1-2).

In the above-mentioned solution, as for the electrospinning, the voltage is 10-15 kv, the receiving distance is 13-18 cm, and the advancing speed is 0.03-0.05 mm/min.

Preferably, an antibiotic or growth factor accounting for 1-5 wt % of the total mass of polyvinyl alcohol, sodium alginate and hydroxyapatite is also added into the spinning solution.

Application of the polyvinyl alcohol/sodium alginate/hydroxyapatite composite fibrous membrane as a soft tissue injury repair dressing is also disclosed.

Compared with the prior art, the present invention has the following beneficial effects: under the condition of not introducing other substances, a combination of sodium alginate and an ultrasonic method is utilized to disperse hydroxyapatite in water stably and uniformly, thereby solving the problem that the hydroxyapatite is prone to agglomeration; By using the electrospinning method and the organic/inorganic nano composite technology, the favorable properties of natural polymer and synthetic polymer materials are organically combined and the composite fibrous membrane is prepared with the biocompatibility of the natural and synthetic polymers and the bioactivity of the hydroxyapatite nanoparticles. The composite fibrous membrane can be used as a soft tissue injury repair dressing and can carry an antibiotic or growth factor to enhance the repair effect of soft tissue injuries.

DESCRIPTION OF THE EMBODIMENTS

Figure 1A:
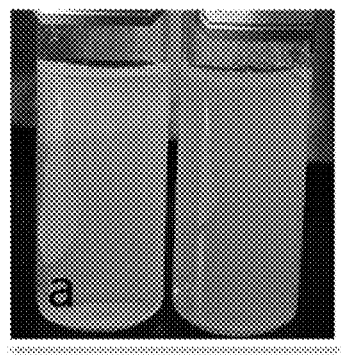
FIG. 1a to FIG. 1e are photographs of the sedimentation of a sodium-alginate-stabilized hydroxyapatite suspension and an untreated hydroxyapatite dispersion over time according to the embodiment 1 of the present invention.
Figure 1B:
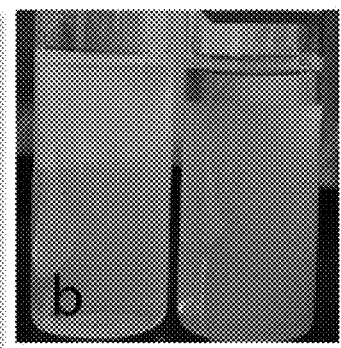
Figure 1C:
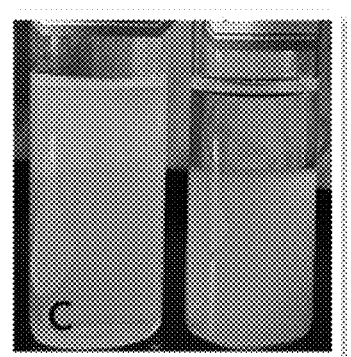
Figure 1D:
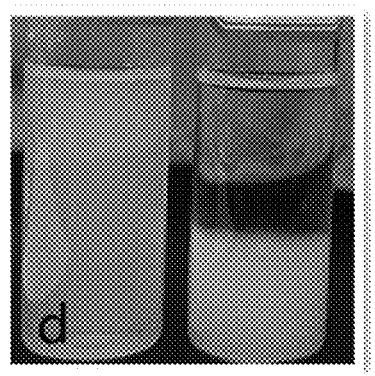
Figure 1E:
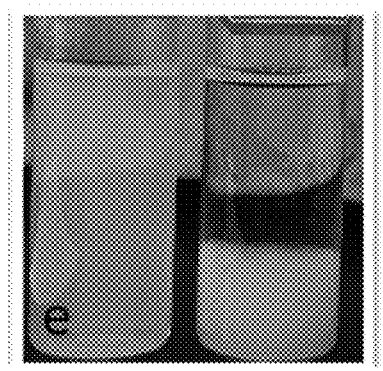

To enable those skilled in the art to fully understand the technical solutions and beneficial effects of the present invention, further descriptions will be given below in conjunction with specific embodiments and accompanying drawings. It should be understood that the following embodiments are merely preferred embodiments of the present invention and are not intended to limit the present invention.

The present invention provides a polyvinyl alcohol/sodium alginate/hydroxyapatite composite fibrous membrane and a preparation method thereof. The preparation method specifically includes the following steps:

Firstly, preparing a diammonium hydrogen phosphate solution of which the concentration is 0.001-0.1 mol/L and a calcium nitrate solution of which the concentration is 0.00668-0.167 mol/L, quickly pouring the diammonium hydrogen phosphate water solution into the calcium nitrate water solution according to a Ca/P mole ratio of 1.67, dropwisely adding ammonia water into the mixture to regulate the pH of the solution to 9-10, stirring the solution uniformly, allowing the solution to react at 80° C., performing centrifugal separation, and performing water washing several times to obtain a hydroxyapatite white precipitate; dispersing the hydroxyapatite white precipitate in deionized water, adding sodium alginate, and performing ultrasonic dispersion to obtain a sodium-alginate-stabilized hydroxyapatite suspension, wherein the concentration of sodium alginate is 0.04-0.15 mg/mL and the concentration of hydroxyapatite is 1.67-16.7 mg/mL.

Secondly, separately preparing a sodium alginate solution of which the mass fraction is 2% and a polyvinyl alcohol solution of which the mass fraction is 18% using the sodium-alginate-stabilized hydroxyapatite suspension at 60-80° C., wherein the hydroxyapatite concentration of the two solutions is 1.67-16.7 mg/mL.

Finally, uniformly mixing the hydroxyapatite-containing sodium alginate solution and the hydroxyapatite-containing polyvinyl alcohol solution in a volume ratio of (0.1-1):(1-2) to obtain a spinning solution containing hydroxyapatite, sodium alginate and polyvinyl alcohol, and performing electrospinning to obtain the composite fibrous membrane, wherein the technological parameters of the electrospinning are: the voltage is 10-15 kv, the receiving distance is 13-18 cm, and the advancing speed is 0.03-0.05 mm/min. The mass ratio of polyvinyl alcohol to sodium alginate to hydroxyapatite in the composite fibrous membrane prepared according to the method of the present invention is 1:(0.01-0.0563):(0.01-0.0834). The composite fibrous membrane can be used as a soft tissue injury repair dressing, and the repair effect of soft tissue injuries can be enhanced by adding an antibiotic or growth factor into the spinning solution.

Embodiment 1

1) Firstly, separately preparing a calcium nitrate water solution of which the concentration is 0.0334 mol/L and a diammonium hydrogen phosphate water solution of which the concentration is 0.02 mol/L; quickly pouring 20 mL of the diammonium hydrogen phosphate water solution into 20 mL of the calcium nitrate water solution according to a Ca/P mole ratio of 1.67, dropwisely adding ammonia water into the mixture to regulate the pH of the solution to 9-10, and stirring and mixing the mixture uniformly; allowing the mixture to react for 1 h while keeping the reaction temperature at 80° C., and repeatedly performing centrifugation three times with deionized water to obtain a white precipitate; redispersing the white precipitate in 40 mL of deionized water to obtain a hydroxyapatite dispersion solution of which the concentration is 1.67 mg/mL, and taking 20 mL of the dispersion solution for later use; and taking 10 mL of deionized water and 0.1 g of sodium alginate to prepare a sodium alginate solution of which the mass fraction is 1%, adding 0.08 mL of the sodium alginate solution into 20 mL of the hydroxyapatite dispersion solution, and uniformly mixing the mixture by applying ultrasonic for 30 s to obtain a sodium-alginate-stabilized hydroxyapatite suspension.

2) Taking two parts of 10 ml of the hydroxyapatite suspension obtained in the step 1), respectively adding 0.2 g of sodium alginate and 1.8 g of polyvinyl alcohol, and allowing sodium alginate and polyvinyl alcohol to dissolve at 80° C. to obtain a sodium alginate (SA) solution of which the mass fraction is 2% and a polyvinyl alcohol (PVA) solution of which the mass fraction is 18%, wherein the hydroxyapatite concentration of the two solutions is 1.67 mg/mL.

3) Taking 2 mL of the 2% SA solution and 6 mL of the 18% PVA solution, uniformly mixing the SA solution and the PVA solution, and performing electrospinning under the conditions of 12 kv voltage, 15 cm receiving distance and 0.04 mm/min advancing speed to obtain a polyvinyl alcohol/sodium alginate/hydroxyapatite fibrous membrane. The mass ratio of polyvinyl alcohol to sodium alginate to hydroxyapatite in the composite fibrous membrane is 1:0.037:0.0124.

Photographs of the sedimentation of the sodium-alginate-stabilized hydroxyapatite suspension and an untreated hydroxyapatite dispersion over time in the step (1) of this embodiment are shown in FIG. 1a to FIG. 1e, wherein the photograph of the sodium-alginate-stabilized hydroxyapatite suspension is on the left side, the photograph of the untreated hydroxyapatite dispersion solution is on the right side, and FIG. 1a, FIG. 1b, FIG. 1c, FIG. 1d and FIG. 1e respectively represent the photographs after 0 h, 1 h, 2 h, 5 h and 24 h of standing. It can be clearly seen from the comparison that the untreated hydroxyapatite dispersion solution has obvious sedimentation within a short period of time due to the fact that hydroxyapatite is particularly prone to agglomeration, and the sodium-alginate-stabilized hydroxyapatite suspension can stay stable for a long time.

Figure 2:
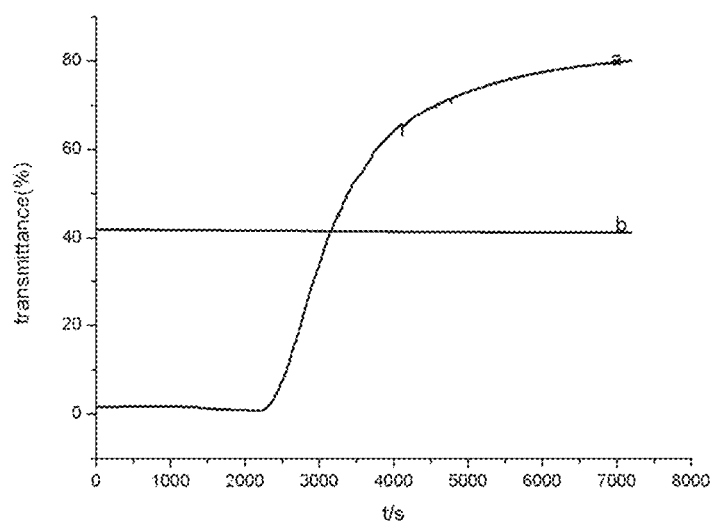
FIG. 2 is a time history plot of the transmittance of the sodium-alginate-stabilized hydroxyapatite suspension and the untreated hydroxyapatite dispersion according to the embodiment 1 of the present invention.

A time history plot of the transmittance of the sodium-alginate-stabilized hydroxyapatite suspension and the untreated hydroxyapatite dispersion in the step (1) of this embodiment is shown in FIG. 2. It can be clearly seen from the drawing that the untreated hydroxyapatite dispersion solution (Curve a) has a serious change in the transmittance with time due to instability of the suspension caused by the agglomeration of particles, and thus, it can be concluded that the sodium-alginate-stabilized hydroxyapatite suspension is much more stable than the untreated hydroxyapatite dispersion solution.

Figure 3:
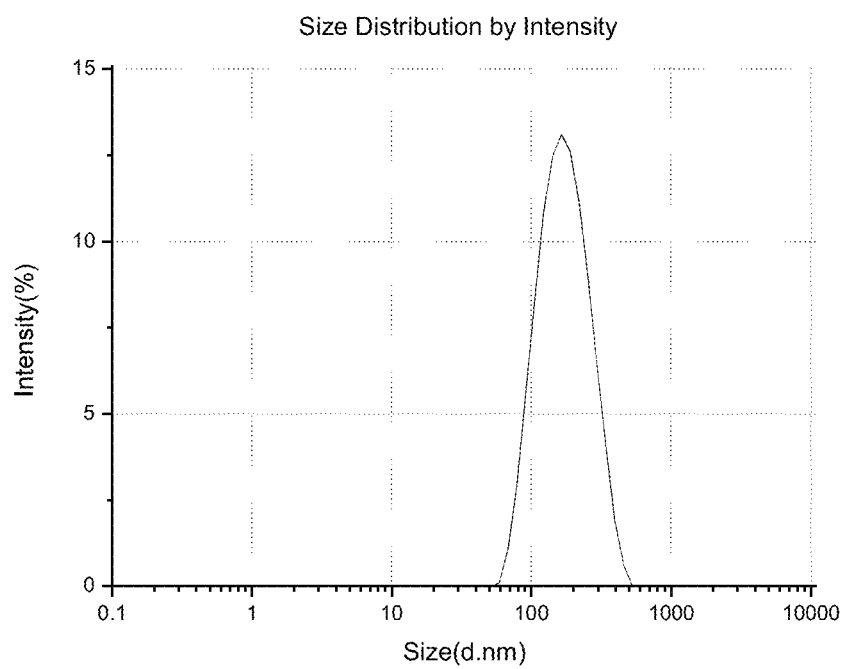
FIG. 3 is a particle size diagram of the sodium-alginate-stabilized hydroxyapatite suspension according to the embodiment 1 of the present invention.

It can be seen from a particle size diagram of the sodium-alginate-stabilized hydroxyapatite suspension (FIG. 3) in this embodiment that the average particle size of the obtained hydroxyapatite is 148 nm, which also indicates that the hydroxyapatite is well dispersed.

Embodiment 2

1) Firstly, separately preparing a calcium nitrate water solution of which the concentration is 0.0334 mol/L and a diammonium hydrogen phosphate water solution of which the concentration is 0.02 mol/L; quickly pouring 20 mL of the diammonium hydrogen phosphate water solution into 20 mL of the calcium nitrate water solution according to a Ca/P mole ratio of 1.67, dropwisely adding ammonia water into the mixture to regulate the pH of the solution to 9-10, and stirring and mixing the mixture uniformly; allowing the mixture to react for 1 h while keeping the reaction temperature at 80° C., and repeatedly performing centrifugation three times with deionized water to obtain a white precipitate; redispersing the white precipitate in 40 mL of deionized water to obtain a hydroxyapatite dispersion solution of which the concentration is 1.67 mg/mL, and taking 20 mL of the dispersion solution for later use; and taking 10 mL of deionized water and 0.1 g of sodium alginate to prepare a sodium alginate solution of which the mass fraction is 1%, adding 0.08 mL of the sodium alginate solution into 20 mL of the hydroxyapatite dispersion solution, and uniformly mixing the mixture by applying ultrasonic for 30 s to obtain a sodium-alginate-stabilized hydroxyapatite suspension.

2) Taking two parts of 10 ml of the hydroxyapatite suspension obtained in the step 1), respectively adding 0.2 g of sodium alginate and 1.8 g of polyvinyl alcohol, and allowing sodium alginate and polyvinyl alcohol to dissolve at 80° C. to obtain a sodium alginate (SA) solution of which the mass fraction is 2% and a polyvinyl alcohol (PVA) solution of which the mass fraction is 18%, wherein the hydroxyapatite concentration of the two solutions is 1.67 mg/mL.

3) Taking 2 mL of the 2% SA solution and 4 mL of the 18% PVA solution, uniformly mixing the SA solution and the PVA solution, and performing electrospinning under the conditions of 12 kv voltage, 15 cm receiving distance and 0.04 mm/min advancing speed to obtain a polyvinyl alcohol/sodium alginate/hydroxyapatite fibrous membrane. The mass ratio of polyvinyl alcohol to sodium alginate to hydroxyapatite in the composite fibrous membrane is 1:0.056:0.0139.

Figure 4:
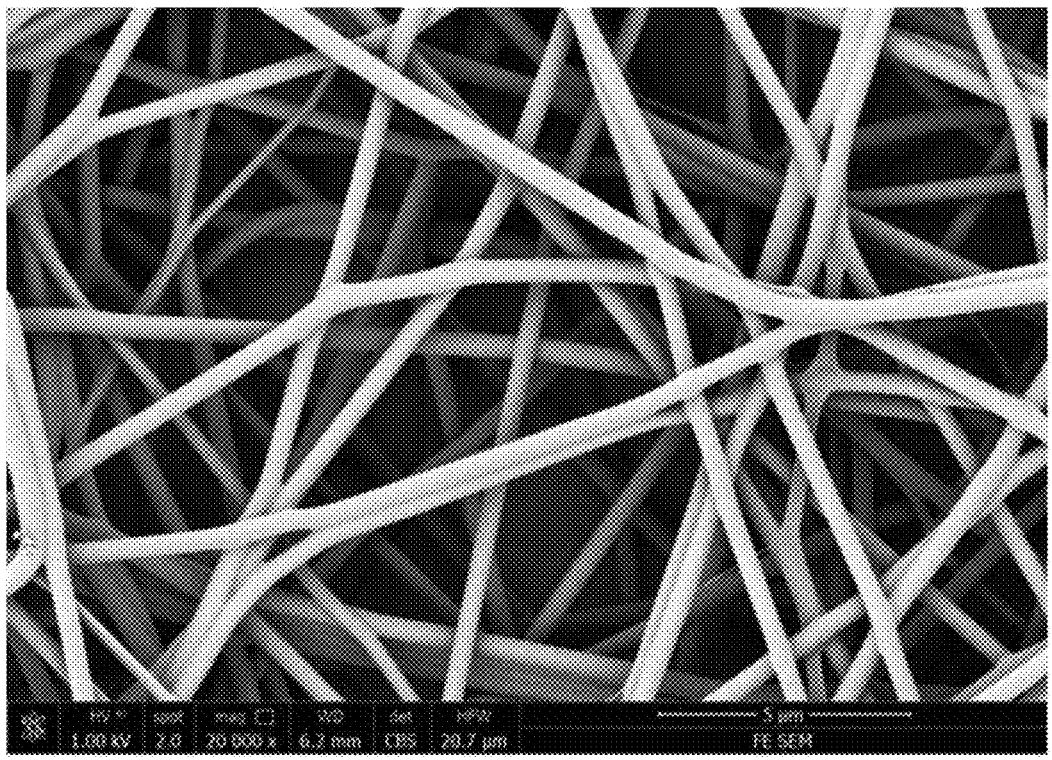
FIG. 4 is a scanning electron microscope image of a composite fibrous membrane prepared according to the embodiment 2 of the present invention.

A scanning electron microscope image of the polyvinyl alcohol/sodium alginate/hydroxyapatite composite fibrous membrane prepared according to this embodiment is shown in FIG. 4, and it can be seen from the image that the composite fibers have favorable appearance.

Embodiment 3

1) Firstly, separately preparing a calcium nitrate water solution of which the concentration is 0.0334 mol/L and a diammonium hydrogen phosphate water solution of which the concentration is 0.02 mol/L; quickly pouring 60 mL of the diammonium hydrogen phosphate water solution into 60 mL of the calcium nitrate water solution according to a Ca/P mole ratio of 1.67, dropwisely adding ammonia water into the mixture to regulate the pH of the solution to 9-10, and stirring and mixing the mixture uniformly; allowing the mixture to react for 1 h while keeping the reaction temperature at 80° C., and repeatedly performing centrifugation three times with deionized water to obtain a white precipitate; redispersing the white precipitate in 20 mL of deionized water to obtain a hydroxyapatite dispersion solution of which the concentration is 10.02 mg/mL for later use; and taking 10 mL of deionized water and 0.1 g of sodium alginate to prepare a sodium alginate solution of which the mass fraction is 1%, adding 0.2 mL of the sodium alginate solution into 20 mL of the hydroxyapatite dispersion solution, and uniformly mixing the mixture by applying ultrasonic for 30 s to obtain a sodium-alginate-stabilized hydroxyapatite suspension.

2) Taking two parts of 10 ml of the hydroxyapatite suspension obtained in the step 1), respectively adding 0.2 g of sodium alginate and 1.8 g of polyvinyl alcohol, and allowing sodium alginate and polyvinyl alcohol to dissolve at 80° C. to obtain a sodium alginate (SA) solution of which the mass fraction is 2% and a polyvinyl alcohol (PVA) solution of which the mass fraction is 18%, wherein the hydroxyapatite concentration of the two solutions is 10.02 mg/mL.

3) Taking 2 mL of the 2% SA solution and 4 mL of the 18% PVA solution, uniformly mixing the SA solution and the PVA solution, and performing electrospinning under the conditions of 12 kv voltage, 15 cm receiving distance and 0.04 mm/min advancing speed to obtain a polyvinyl alcohol/sodium alginate/hydroxyapatite fibrous membrane. The mass ratio of polyvinyl alcohol to sodium alginate to hydroxyapatite in the composite fibrous membrane is 1:0.056:0.0834.

Figure 5:
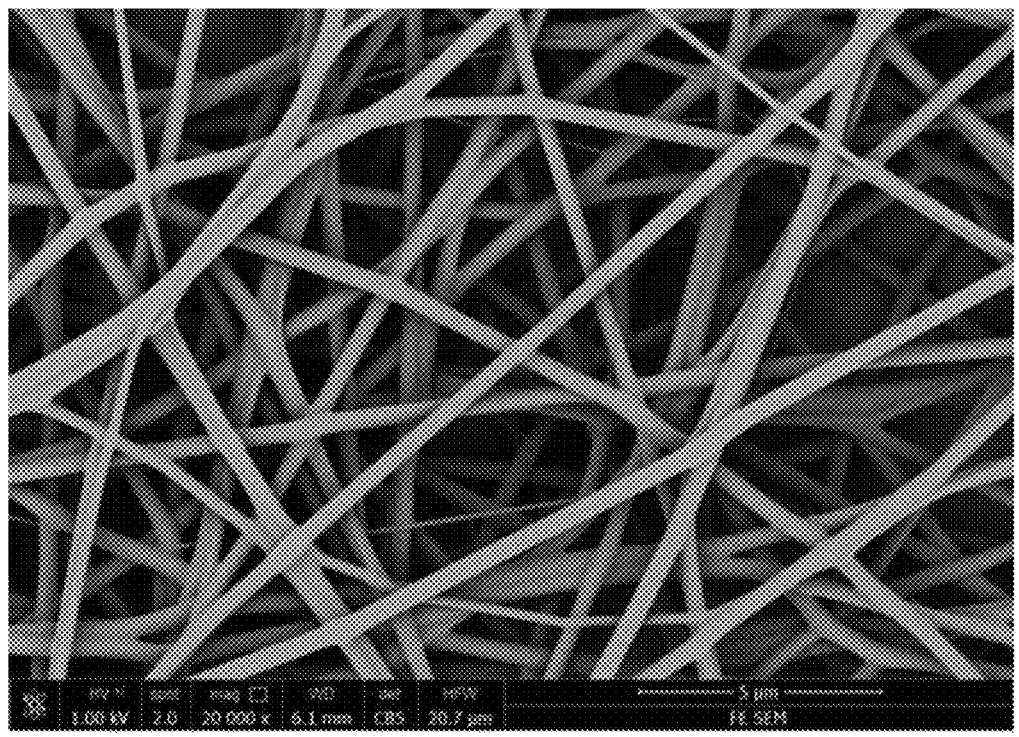
FIG. 5 is a scanning electron microscope image of a composite fibrous membrane prepared according to the embodiment 3 of the present invention.

A scanning electron microscope image of the polyvinyl alcohol/sodium alginate/hydroxyapatite composite fibrous membrane prepared according to this embodiment is shown in FIG. 5, and it can be seen from the image that the composite fibers have favorable appearance.

Embodiment 4

1) Firstly, separately preparing a calcium nitrate water solution of which the concentration is 0.0334 mol/L and a diammonium hydrogen phosphate water solution of which the concentration is 0.02 mol/L; quickly pouring 20 mL of the diammonium hydrogen phosphate water solution into 20 mL of the calcium nitrate water solution according to a Ca/P mole ratio of 1.67, dropwisely adding ammonia water into the mixture to regulate the pH of the solution to 9-10, and stirring and mixing the mixture uniformly; allowing the mixture to react for 1 h while keeping the reaction temperature at 80° C., and repeatedly performing centrifugation three times with deionized water to obtain a white precipitate; redispersing the white precipitate in 40 mL of deionized water to obtain a hydroxyapatite dispersion solution of which the concentration is 1.67 mg/mL, and taking 20 mL of the hydroxyapatite dispersion solution for later use; and taking 10 mL of deionized water and 0.1 g of sodium alginate to prepare a sodium alginate solution of which the mass fraction is 1%, adding 0.08 mL of the sodium alginate solution into 20 mL of the dispersion solution, and uniformly mixing the mixture by applying ultrasonic for 30 s to obtain a sodium-alginate-stabilized hydroxyapatite suspension.

2) Taking two parts of 10 ml of the hydroxyapatite suspension obtained in the step 1), respectively adding 0.2 g of sodium alginate and 1.8 g of polyvinyl alcohol, and allowing sodium alginate and polyvinyl alcohol to dissolve at 80° C. to obtain a sodium alginate (SA) solution of which the mass fraction is 2% and a polyvinyl alcohol (PVA) solution of which the mass fraction is 18%, wherein the hydroxyapatite concentration of the two solutions is 1.67 mg/mL.

3) Taking 2 mL of the 2% SA solution and 4 mL of the 18% PVA solution, mixing the SA solution and the PVA solution, adding 5% (0.0385 g) tetracycline hydrochloride, uniformly mixing the mixture, and performing electrospinning under the conditions of 12 kv voltage, 15 cm receiving distance and 0.04 mm/min advancing speed to obtain a tetracycline-hydrochloride-carried polyvinyl alcohol/sodium alginate/hydroxyapatite fibrous membrane. The mass ratio of polyvinyl alcohol to sodium alginate to hydroxyapatite to tetracycline hydrochloride in the composite fibrous membrane is 1:0.056:0.0139:0.0535.

Figure 6:
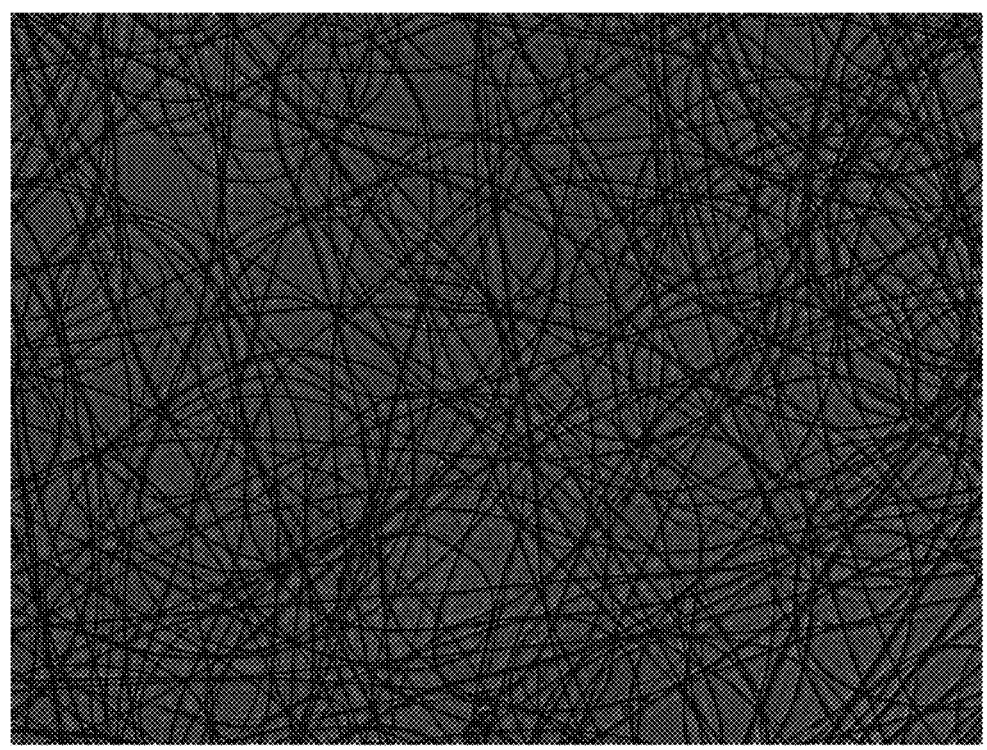
FIG. 6 is an optical micrograph of a composite fibrous membrane prepared according to the embodiment 4 of the present invention.
Figure 7:
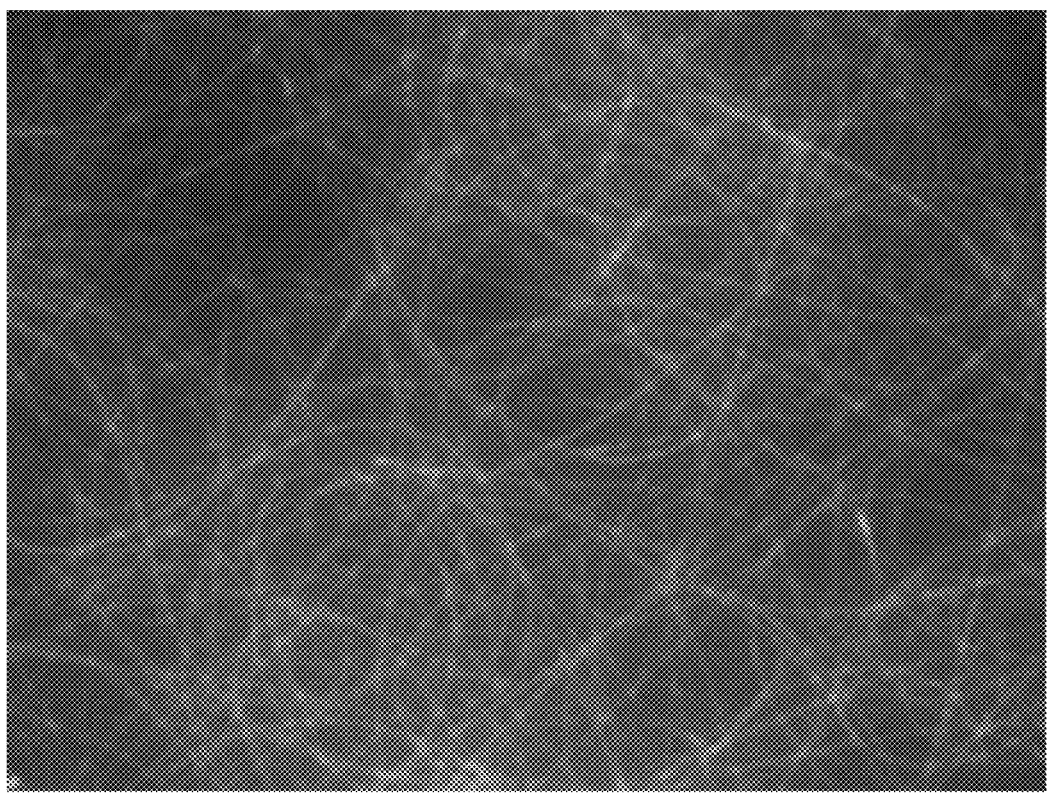
FIG. 7 is a fluorescence microscope image of the composite fibrous membrane prepared according to the embodiment 4 of the present invention.

An optical micrograph and a fluorescence microscope image of the polyvinyl alcohol/sodium alginate/hydroxyapatite composite fibrous membrane prepared according to this embodiment are shown in FIG. 6 and FIG. 7. It can be seen from the optical micrograph of the composite fibrous membrane that the fibers have favorable appearance, and it can be seen from the fluorescence microscope image of the composite fibrous membrane that the tetracycline hydrochloride has been successfully carried into the composite fibrous membrane due to the peculiar fluorescence of the tetracycline hydrochloride.

What is claimed is:

1. A preparation method of a polyvinyl alcohol/sodium alginate/hydroxyapatite composite fibrous membrane, consisting of the following steps:
    (a) reacting a diammonium hydrogen phosphate with a calcium nitrate to prepare a hydroxyapatite, dispersing the hydroxyapatite in deionized water, adding a first sodium alginate as a stabilizer to the hydroxyapatite dispersed in deionized water, and after adding the first sodium alginate uniformly mixing by ultrasonic dispersion to obtain a sodium-alginate-stabilized hydroxyapatite suspension;
    (b) after obtaining the sodium-alginate-stabilized hydroxyapatite suspension, dividing the sodium-alginate-stabilized hydroxyapatite suspension into a first hydroxyapatite suspension and a second hydroxyapatite suspension, preparing a hydroxyapatite-suspending sodium alginate suspension by adding a second sodium alginate into the first hydroxyapatite suspension prepared in the step (a), and preparing a hydroxyapatite-suspending polyvinyl alcohol suspension by adding polyvinyl alcohol into the second hydroxyapatite suspension prepared in the step (a); and
    (c) proportionally and uniformly mixing the hydroxyapatite-suspending sodium alginate suspension and the hydroxyapatite-suspending polyvinyl alcohol suspension to obtain a spinning composition containing the suspended hydroxyapatite, the first sodium alginate, the second sodium alginate and the polyvinyl alcohol, and performing electrospinning to obtain the composite fibrous membrane,
    wherein a concentration of the first sodium alginate in the sodium-alginate-stabilized hydroxyapatite suspension is 0.04-0.15 mg/mL, and a concentration of the hydroxyapatite in the sodium-alginate-stabilized hydroxyapatite suspension is 1.67-16.7 mg/mL, wherein the hydroxyapatite is nanoparticle, the mass ratio of polyvinyl alcohol to sodium alginate to hydroxyapatite in the composite fibrous membrane is 1:(0.01-0.0563):(0.01-0.0834), and the preparation method prevents agglomeration of the hydroxyapatite, wherein the hydroxyapatite in the Sodium-alginate stabilized hydroxyapatite suspension is uniformly dispersed and no agglomeration and sedimentation occur in the deionized water containing the first sodium alginate.

2. The preparation method of the polyvinyl alcohol/sodium alginate/hydroxyapatite composite fibrous membrane according to claim 1, wherein the process of preparing the hydroxyapatite comprises the following steps: pouring a diammonium hydrogen phosphate water solution containing the diammonium hydrogen phosphate into a calcium nitrate water solution containing the calcium nitrate according to a Ca/P mole ratio of 1.67, dropwisely adding an ammonia water into the mixture to regulate the pH of the solution to 9-10, stirring the mixture uniformly, allowing the mixture to react at 80° C., performing centrifugal separation, and performing water washing several times to obtain the hydroxyapatite white precipitate.

3. The preparation method of the polyvinyl alcohol/sodium alginate/hydroxyapatite composite fibrous membrane according to claim 2, wherein the concentration of the diammonium hydrogen phosphate water solution is 0.001-0.1 mol/L, and the concentration of the calcium nitrate water solution is 0.00668-0.167 mol/L.

4. The preparation method of the polyvinyl alcohol/sodium alginate/hydroxyapatite composite fibrous membrane according to claim 3, wherein an antibiotic or a growth factor accounting for 1-5 wt % of the total mass of polyvinyl alcohol, sodium alginate and hydroxyapatite is also added into the spinning composition.

5. The preparation method of the polyvinyl alcohol/sodium alginate/hydroxyapatite composite fibrous membrane according to claim 2, wherein an antibiotic or a growth factor accounting for 1-5 wt % of the total mass of polyvinyl alcohol, sodium alginate and hydroxyapatite is also added into the spinning composition.

6. The preparation method of the polyvinyl alcohol/sodium alginate/hydroxyapatite composite fibrous membrane according to claim 1, wherein the hydroxyapatite-suspending sodium alginate suspension of which the mass fraction of the second sodium alginate is 2% and the hydroxyapatite-suspending polyvinyl alcohol suspension of which the mass fraction of the polyvinyl alcohol is 18% are prepared at 60-80° C.

7. The preparation method of the polyvinyl alcohol/sodium alginate/hydroxyapatite composite fibrous membrane according to claim 6, wherein an antibiotic or a growth factor accounting for 1-5 wt % of the total mass of polyvinyl alcohol, sodium alginate and hydroxyapatite is also added into the spinning composition.

8. The preparation method of the polyvinyl alcohol/sodium alginate/hydroxyapatite composite fibrous membrane according to claim 1, wherein the volume ratio of the hydroxyapatite-suspending sodium alginate suspension to the hydroxyapatite-suspending polyvinyl alcohol suspension during the mixing is (0.1-1):(1-2).

9. The preparation method of the polyvinyl alcohol/sodium alginate/hydroxyapatite composite fibrous membrane according to claim 8, wherein an antibiotic or a growth factor accounting for 1-5 wt % of the total mass of polyvinyl alcohol, sodium alginate and hydroxyapatite is also added into the spinning composition.

10. The preparation method of the polyvinyl alcohol/sodium alginate/hydroxyapatite composite fibrous membrane according to claim 1, wherein as for the electrospinning, the voltage is 10-15 kv, and the receiving distance is 13-18 cm.

11. The preparation method of the polyvinyl alcohol/sodium alginate/hydroxyapatite composite fibrous membrane according to claim 10, wherein an antibiotic or a growth factor accounting for 1-5 wt % of the total mass of polyvinyl alcohol, sodium alginate and hydroxyapatite is also added into the spinning composition.

12. The preparation method of the polyvinyl alcohol/sodium alginate/hydroxyapatite composite fibrous membrane according to claim 1, wherein an antibiotic or a growth factor accounting for 1-5 wt % of the total mass of polyvinyl alcohol, sodium alginate and hydroxyapatite is also added into the spinning solution.

* * * * *